(12) United States Patent
Zhuang et al.

(10) Patent No.: US 9,693,439 B1
(45) Date of Patent: Jun. 27, 2017

(54) HIGH BRIGHTNESS LIQUID DROPLET X-RAY SOURCE FOR SEMICONDUCTOR METROLOGY

(71) Applicant: KLA-Tencor Corporation, Milpitas, CA (US)

(72) Inventors: Guorong V. Zhuang, San Jose, CA (US); Michael S. Bakeman, San Jose, CA (US); Andrei V. Shchegrov, Campbell, CA (US); Jonathan M. Madsen, Los Altos, CA (US)

(73) Assignee: KLA-Tencor Corporation, Milpitas, CA (US)

(*) Notice: Subject to any disclaimer, the term of this patent is extended or adjusted under 35 U.S.C. 154(b) by 196 days.

(21) Appl. No.: 14/304,329

(22) Filed: Jun. 13, 2014

Related U.S. Application Data

(60) Provisional application No. 61/837,178, filed on Jun. 20, 2013.

(51) Int. Cl.
*H05G 2/00* (2006.01)
*G01N 23/201* (2006.01)

(52) U.S. Cl.
CPC .......... *H05G 2/005* (2013.01); *G01N 23/201* (2013.01); *H05G 2/008* (2013.01)

(58) Field of Classification Search
CPC ........ H05G 2/001; H05G 2/003; H05G 2/005; H05G 2/008; G01N 23/201; G01N 2223/054; G01N 2223/6116
See application file for complete search history.

(56) References Cited

U.S. PATENT DOCUMENTS

| 4,723,262 A * | 2/1988 | Noda | H05G 2/008 378/119 |
| 6,493,423 B1 * | 12/2002 | Bisschops | H05G 2/003 378/119 |

(Continued)

FOREIGN PATENT DOCUMENTS

CN 103042221 A * 4/2013

OTHER PUBLICATIONS

Fujimoto et al., "Development of Laser-Produced Tin Plasma-Based EUV Light Source Technology for HVM EUV Lithography," Physics Research International, vol. 2012, Article ID 249495, (2012), pp. 1-11.*

(Continued)

*Primary Examiner* — Glen Kao
(74) *Attorney, Agent, or Firm* — Joseph S. Spano; Spano Law Group

(57) ABSTRACT

Methods and systems for realizing a high brightness liquid metal droplet based x-ray source suitable for high throughput x-ray metrology are presented herein. A high power laser bombards a solid target material to generate liquid metal droplets. The laser generated liquid metal droplets are excited with a focused, high power excitation beam such as an electron or laser beam. The excitation beam is synchronized with the stream of liquid metal droplets stimulated by the high power laser to achieve a stable x-ray emission generated by the excited liquid metal droplets. In some embodiments, x-ray optics are designed to efficiently collect and focus radiation within a desired emission band onto a measurement target. Reliability is improved by shielding the excitation source and the x-ray optics from the region of interaction between the excitation beam and the liquid metal droplet anode by a localized curtain of shielding gas.

19 Claims, 9 Drawing Sheets

(56) References Cited

U.S. PATENT DOCUMENTS

| | | | | |
|---|---|---|---|---|
| 7,929,667 B1* | 4/2011 | Zhuang | ............... | H05G 2/005 378/119 |
| 2002/0015473 A1* | 2/2002 | Hertz | ............... | H05G 2/003 378/143 |
| 2005/0041779 A1* | 2/2005 | Michette | ............... | G21K 1/06 378/84 |
| 2013/0301805 A1* | 11/2013 | Hemberg | ............... | H01J 35/08 378/137 |
| 2013/0329204 A1* | 12/2013 | Pellemans | ............... | H05G 2/003 355/67 |
| 2014/0294157 A1* | 10/2014 | Chen | ............... | G01N 23/223 378/145 |

OTHER PUBLICATIONS

Fujimoto, Junichi, et al., "Development of Laser-Produced Tin Plasma-Based EUV Light Source Technology For HVM EUV Lithography," Physics Research International, vol. 2012, Article ID 249495 (2012).

\* cited by examiner

150

| ELEMENT | Mg | Al | Ga | Mo | Ru | Rh | Pd |
|---|---|---|---|---|---|---|---|
| ATOMIC NUMBER | 12 | 13 | 31 | 42 | 44 | 45 | 46 |
| PHOTON ENERGY (keV) | 1.254 | 1.486 | 9.252 | 17.48 | 19.279 | 20.22 | 21.177 |
| X-RAY $\lambda$ (Angstrom) | 9.89 | 8.34 | 1.34 | 0.709 | 0.643 | 0.613 | 0.585 |
| K$\alpha$ (YIELD) | 2.65e-2 | 3.57e-2 | 5.10e-1 | 7.64e-1 | 7.93e-1 | 8.07e-1 | 8.19e-1 |
| L$\alpha$ (YIELD) | 2.9e-5 | 7.5e-2 | 1.2e-2 | 2e-2 | 4e-2 | 4.3e-2 | 4.7e-2 |
| MELTING TEMP (°C) |  | 660 | 31 | 2894 | 2334 | 1966 | 1552 |

| ELEMENT | In | Sn | La | Nd | Gd | W | Re |
|---|---|---|---|---|---|---|---|
| ATOMIC NUMBER | 49 | 50 | 57 | 60 | 64 | 74 | 75 |
| PHOTON ENERGY (keV) | 24.209 | 25.271 | 33.442 | 37.36 | 43.0 | 59.32 | 61.14 |
| X-RAY $\lambda$ (Angstrom) | 0.512 | 0.491 | 0.371 | 0.33 | 0.29 | 0.21 | 0.20 |
| K$\alpha$ (YIELD) | 8.5e-1 | 8.59e-1 | 9.06e-1 | 9.2e-1 | 9.34e-1 | 9.54e-1 | 9.59e-1 |
| L$\alpha$ (YIELD) | 6e-2 | 6.5e-2 | 1e-1 | 1.2e-1 | 1.5e-1 | 2.5e-1 | 2.6e-1 |
| MELTING TEMP (°C) | 157 | 232 | 920 | 1010 | 1312 | 3422 | 3182 |

FIG. 3

HIGH BRIGHTNESS LIQUID DROPLET X-RAY SOURCE FOR SEMICONDUCTOR METROLOGY

CROSS REFERENCE TO RELATED APPLICATION

The present application for patent claims priority under 35 U.S.C. §119 from U.S. provisional patent application Ser. No. 61/837,178, entitled "High Brightness X-ray Source Using Liquid Metal Droplets," filed Jun. 20, 2013, the subject matter of which is incorporated herein by reference in its entirety.

TECHNICAL FIELD

The described embodiments relate to metrology systems and methods, and more particularly to methods and systems for improved illumination.

BACKGROUND INFORMATION

The various features and multiple structural levels of semiconductor devices such as logic and memory devices are typically fabricated by a sequence of processing steps applied to a specimen. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition and other parameters of nanoscale structures.

As devices (e.g., logic and memory devices) move toward smaller nanometer-scale dimensions, characterization becomes more difficult. Devices incorporating complex three-dimensional geometry and materials with diverse physical properties contribute to characterization difficulty. For example, modern memory structures are often high-aspect ratio, three-dimensional structures that make it difficult for optical radiation to penetrate to the bottom layers. In addition, the increasing number of parameters required to characterize complex structures (e.g., FinFETs), leads to increasing parameter correlation. As a result, the parameters characterizing the target often cannot be reliably decoupled with available measurements. In another example, opaque, high-k materials are increasingly employed in modern semiconductor structures. Optical radiation is often unable to penetrate layers constructed of these materials. As a result, measurements with thin-film scatterometry tools such as ellipsometers or reflectometers are becoming increasingly challenging.

In response, more complex optical tools have been developed. For example, tools with multiple angles of illumination, shorter and broader ranges of illumination wavelengths, and more complete information acquisition from reflected signals (e.g., measuring multiple Mueller matrix elements in addition to the more conventional reflectivity or ellipsometric signals) have been developed. However, these approaches have not reliably overcome fundamental challenges associated with measurement of many advanced targets (e.g., complex 3D structures, structures smaller than 10 nm, structures employing opaque materials) and measurement applications (e.g., line edge roughness and line width roughness measurements).

Another response to these recent challenges has been the adoption of x-ray metrology for measurements including film thickness, composition, strain, surface roughness, line edge roughness, and porosity. Many x-ray metrology techniques used in semiconductor manufacturing can benefit from high brightness x-ray sources. For example, critical dimension small angle x-ray scattering (CD-SAXS) measurements often require long integration times due to the low scattering of certain materials. A high brightness source can improve the throughput of CD-SAXS measurements.

X-ray sources including electron beam sources with water cooled targets and solid, rotating anodes have been employed. Another exemplary high brightness X-ray source is a liquid metal jet X-ray source having a liquid metal anode. Unfortunately, for both conventional solid and liquid anode sources, measurement throughput has been impaired by limited power loading on the anode. An increase in power loading of a conventional solid metal anode source causes ablation and destruction of the anode. For typical liquid metal anode sources, an increase in power loading produces excessive metal vapor that damages the cathode. Low melting temperature anode materials have very high metal vapor pressure. Thus, the cathode of the electron gun of the liquid metal jet x-ray source is susceptible to poisoning by liquid metal vapor.

Liquid metal jet sources employ low melting point metals or alloys of low melting point metals. These metals are usually low atomic number elements that emit relatively low energy x-rays (i.e., long wavelength x-rays). These liquid metal anode materials are selected for their low melting point and are maintained in the liquid phase and recollected by a liquid circulation system. This approach is limited to metals or metal alloys that can be sustained in a liquid phase. Thus, the low melting temperature requirement severely limits the available energy range of a liquid metal jet x-ray source suitable for semiconductor metrology.

Future metrology applications present challenges for metrology due to increasingly high resolution requirements, multi-parameter correlation, increasingly complex geometric structures, and increasing use of opaque materials. The adoption of x-ray metrology for semiconductor applications requires improved x-ray sources with the highest possible brightness.

SUMMARY

Methods and systems for realizing a high brightness liquid droplet based x-ray source suitable for high throughput x-ray metrology are presented herein.

In one aspect, a high brightness x-ray source is produced by exciting a laser generated liquid metal droplet anode with a high power excitation source. A high power pulsed laser or a continuous wave (CW) laser bombards a solid target material to generate liquid metal droplets. The laser generated liquid metal droplets are subsequently bombarded by a high power excitation source to generate x-ray radiation.

Two types of high power excitation sources may be contemplated. In some embodiments, a focused high energy electron beam is focused onto the liquid metal droplet anode to stimulate high brightness x-ray emission. In some other embodiments, a high power pulsed laser or a high power CW laser is focused onto the liquid metal droplet anode to stimulate high brightness x-ray emission.

In another aspect, x-ray optics are designed to efficiently focus radiation in the desired emission band. The stimulated x-ray emission includes bremsstrahlung emission and x-ray line emission corresponding to the liquid metal anode material. In some embodiments, the x-ray optics are configured to collect x-ray emission over a range of angles from a surface normal of the liquid metal anode. The range of angles includes an angle of maximum intensity of a superposition of Bremsstrahlung emission and a desired line emission.

In some embodiments, the x-ray optics are configured to focus the radiation of the strongest x-ray line emissions directly onto the sample. In some other embodiments the x-ray optics are configured to direct the radiation of the strongest x-ray line emissions onto a secondary target. The secondary target produces x-ray lines corresponding to its constituent elements. The x-ray emission from the secondary target is subsequently focused onto the specimen.

In yet another aspect, the reliability of a LGLMD x-ray source operating at high excitation beam power density levels at the anode is improved by shielding the excitation source and the x-ray optics from the region of interaction between the excitation beam and the liquid metal droplet anode by a localized curtain of shielding gas (e.g., xenon, argon, etc.).

In yet another aspect, elements of the LGLMD source is configured for active control by a computing system. In one example, the computing system is configured to communicate control signals to the excitation source to synchronize a high power density excitation beam generated by the excitation source with a stream of liquid metal droplets stimulated by the high power laser bombarding the solid anode. In another example, current or voltage supplied to electromagnetic elements of an excitation beam focusing system may be actively controlled. In this manner, the generating, focusing, and directing of an excitation beam is achieved under the control of a computing system to achieve a stable interaction of the excitation beam with the stream of liquid metal droplets. In addition, the focusing and directing of x-ray emission is achieved under the control of a computing system to achieve a stable x-ray beam incident on a specimen under inspection.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

BRIEF DESCRIPTION OF THE DRAWINGS

FIG. 3 illustrates a chart 150 include a number of suitable anode materials.

DETAILED DESCRIPTION

Reference will now be made in detail to background examples and some embodiments of the invention, examples of which are illustrated in the accompanying drawings.

Systems employed to measure structural and material characteristics (e.g., material composition, dimensional characteristics of structures and films, etc.) associated with different semiconductor fabrication processes based on x-ray illumination are presented. More specifically, methods and systems for realizing a high brightness laser generated liquid metal droplet (LGLMD) x-ray source suitable for high throughput x-ray metrology are presented herein.

In one aspect, a high brightness x-ray source is produced by exciting a laser generated liquid metal droplet anode with a high power excitation source. A high power pulsed laser or a continuous wave (CW) laser bombards a solid target material to generate the liquid metal droplets. The laser generated liquid metal droplets are subsequently bombarded by a high power excitation source to generate x-ray radiation.

Two types of high power excitation sources may be contemplated. In some embodiments, a focused high energy electron beam is focused onto the liquid metal droplet anode to stimulate high brightness x-ray emission. In some other embodiments, a high power pulsed laser or a high power CW laser is focused onto the liquid metal droplet anode to stimulate high brightness x-ray emission.

In another aspect, x-ray optics are designed to efficiently focus radiation in the desired emission band. The stimulated x-ray emission includes bremsstrahlung emission and x-ray line emission corresponding to the liquid metal anode material. In some embodiments, the x-ray optics are configured to direct the radiation of the strongest x-ray line emissions to the sample. In some other embodiments the x-ray optics are configured to direct the radiation of the strongest x-ray line emissions onto a secondary target. The secondary target produces x-ray lines corresponding to its constituent elements. A secondary target can be used to reduce bremsstrahlung emission in applications such as XRF. The x-ray emission from the secondary target is subsequently focused onto the specimen.

In yet another aspect, the reliability of a LGLMD x-ray source operating at high excitation beam power density levels at the anode is improved by shielding the excitation source and the x-ray optics from the region of interaction between the excitation beam and the liquid metal droplet anode by a localized curtain of shielding gas (e.g., xenon, argon, etc.).

Figure 1:
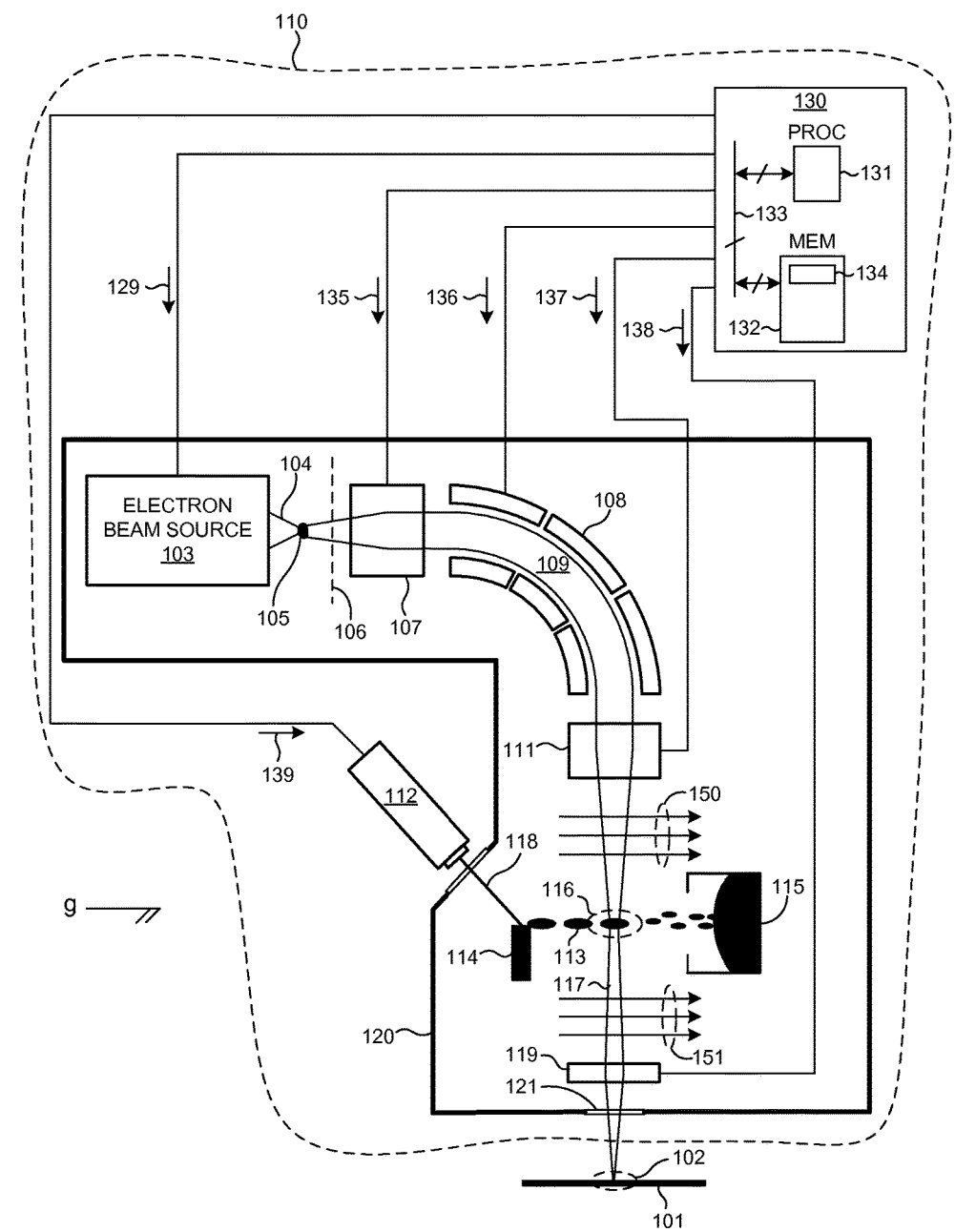
FIG. 1 is a diagram illustrative of a laser generated liquid metal droplet (LGLMD) x-ray source 110 in at least one novel aspect.

FIG. 1 illustrates an embodiment of a laser generated liquid metal droplet (LGLMD) x-ray source 110 in at least one novel aspect. In the depicted embodiment, LGLMD x-ray source 110 delivers high brightness x-ray illumination to a specimen 101 over an inspection area 102. In some embodiments, the inspection area 102 has a spot size of fifty micrometers or less.

In the embodiment depicted in FIG. 1, LGLMD x-ray source 110 includes an electron beam source 103 (e.g., electron gun) configured to generate electron emission 105 from a cathode 104. In the depicted embodiment, electron beam source 103 includes a low noise voltage supply configured to generate a low noise, controlled voltage between cathode 104 and a grating 106 (e.g., less than approximately 10 kV). The resulting low noise electric field between cathode 104 and grating 106 promotes a stable emission of free electrons 105 from cathode 105 and a steady drift of those electrons away from cathode 105 toward grating 106. In some embodiments, the electron beam source 103 is configured to generate a continuous electron beam. In some other embodiments, the electron beam source 103 is configured to generate a pulsed electron beam.

In one aspect, a voltage supply (not shown) is configured to generate a large voltage difference between grating 106 and liquid metal anode 113 to accelerate a stream of focused electrons 109 from grating 106 to liquid metal anode 113. In some embodiments, a voltage difference between the cathode 104 and the liquid metal anode 113 is greater than 100 kV. An acceleration voltage greater than 100 kV enables a stream of electrons 109 having an electron power density greater than 1,000 kW/mm2 at the liquid metal anode 113. This results in a compact x-ray source with higher brightness.

In the embodiment depicted in FIG. 1, LGLMD x-ray source 110 includes electron optics 107 configured to focus the stream of electrons 109 emitted from the cathode and direct the stream of electrons 109 toward beam bending optics 108. Beam bending optics 108 are configured to redirect the stream of electrons 109 such that the cathode 104 is out of any line of sight of the region of impact 116 of the stream of electrons 109 with the liquid metal anode 113. In this manner, metal vapor generated by the interaction of the electron beam with the liquid metal does not have a direct flight path to the cathode. Without a direct flight path, the probability that a particular amount of metal vapor will reach the cathode before adhering to another surface is significantly diminished.

After passing through beam bending optics 108, the stream of electrons 109 passes through electron optics 111. Electron optics 111 are configured to direct and/or focus the stream of electrons 109 toward the liquid metal anode 113.

Electron optics 107, 108, and 111 include suitable electromagnets, permanent magnets, or any combination of electromagnets and permanent magnets for focusing the electron beam and directing the stream of electrons 109. In some embodiments, electron optics 107, 108, and 111 may include solenoids, quadrupole lenses such as Halbach cylinders or electrostatic elements such as Einzel lenses to focus and direct the electron beam. In addition, any of electron optics 107, 108 and 111 can be configured as an electron monochromator. Moreover, any of electron optics 107, 108, and 111 may be employed to focus the beam to further reduce electron beam noise.

In addition, any of electron optics 107, 108, and 111 may be configured for active control by computing system 130. As depicted in FIG. 1, computing system 130 is coupled to electron optics 107, 108, and 111. Command signals 135, 136, and 137 are communicated to electron optics 107, 108, and 111, respectively. For example, current or voltage supplied electromagnetic elements may be actively controlled based on any of command signals 135, 136, and 137. In another example, the position of a magnetic element (e.g., a permanent magnet) may be manipulated by a positioning system (not shown) based on any of command signals 135, 136, and 137. In this manner, the focusing and directing of the stream of electrons 109 is achieved under the control of computing system 130 to achieve a stable stream of electrons 109 incident on liquid metal anode 113.

In the embodiment depicted in FIG. 1, LGLMD 101 includes an electron beam excitation source. However, other embodiments of LGLMD 101 may include an optical excitation source that generates a high energy laser beam that interacts with the liquid metal droplets to generate x-ray emission. In some embodiments, a high energy femtosecond laser source is employed along with focusing optics to focus the laser beam as tightly as possible on the stream of liquid metal droplets 113. An optical excitation source may be desirable to relax the vacuum requirements. Although, an optical excitation beam may benefit from transmission through vacuum (i.e., reduced disturbances and losses), in general, the vacuum requirements in the region of transmission for the optical excitation beam are significantly reduced compared to an electron excitation beam. However, an electron beam has a much shorter De Broglie wavelength, and thus, is much more easily focused than an optical excitation beam.

In one aspect, any of the electron beam source 103 including cathode 104, electron optics 107, 108, and 111, x-ray optics 119, and other components are shielded from the interaction of the stream of electrons 109 and the liquid metal anode 113 by a localized gas curtain. In the embodiment depicted in FIG. 1, a localized gas curtain 150 separates the cathode and electron optics from the region of interaction 116 between the electron beam 109 and the liquid metal anode 113. Similarly, a localized gas curtain 151 separates the x-ray optics 119 from the region of interaction 116 between the electron beam 109 and the liquid metal anode 113.

Figure 7:
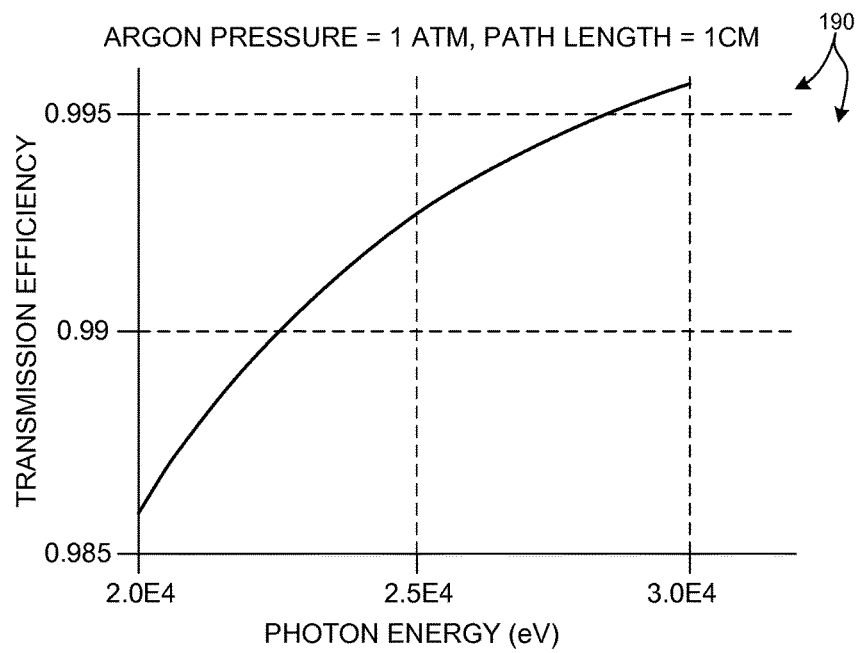
FIG. 7 illustrates a plot 190 of transmission efficiency of x-rays through a curtain of Argon gas having a thickness of one centimeter at a pressure of one atmosphere.
Figure 8:
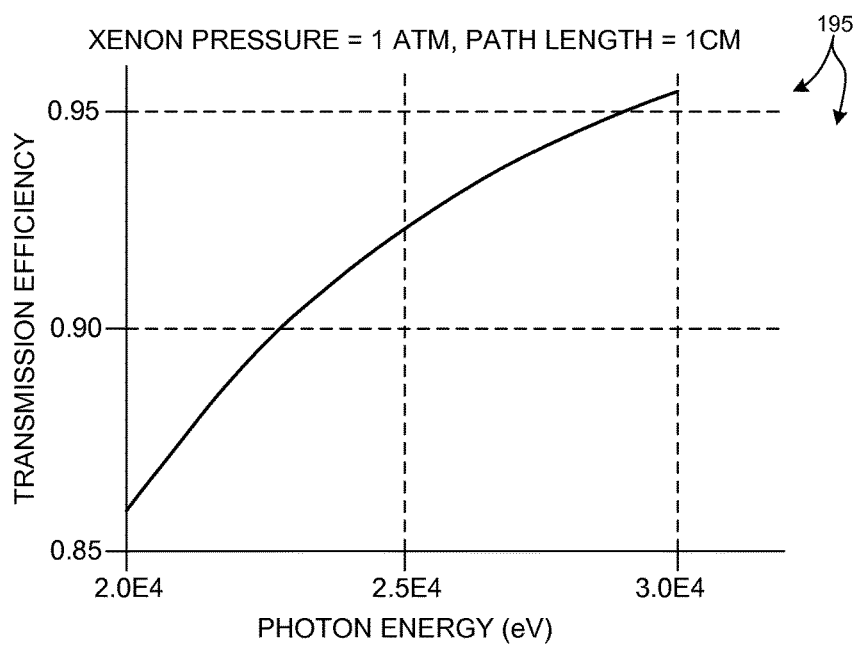
FIG. 8 illustrates a plot 195 of transmission efficiency of x-rays through a curtain of Xenon gas having a thickness of one centimeter at a pressure of one atmosphere.

The localized gas curtain includes an inert gas jet of high atomic weight (e.g., Argon, Xenon, etc.) to mitigate debris generated by the interaction between the electron beam 109 and the liquid metal anode 113. The pressure of the gas curtain is high enough to deflect debris (e.g., high energy metal ions, solidified metal particles, etc.) and act as a barrier to reduce metal vapor poisoning of cathode 104, but not so high as to deflect or attenuate the high energy electron beam. The gas curtain should attenuate the x-ray emission as little as possible. FIG. 7 illustrates a plot 190 of transmission efficiency of x-rays through a curtain of Argon gas having a thickness of one centimeter at a pressure of one atmosphere. As depicted, x-rays having energy greater than 22.5 keV are transmitted through the Argon gas curtain with an efficiency greater than 99%. FIG. 8 illustrates a plot 195 of transmission efficiency of x-rays through a curtain of Xenon gas having a thickness of one centimeter at a localized pressure of one atmosphere. As depicted, x-rays having an energy greater than 22.5 keV are transmitted through the Xenon gas curtain with an efficiency greater than 90%.

In some embodiments, the localized gas curtain is configured as a gas jet that is differentially pumped within a vacuum environment. By placing the gas jet close to the localized pump, a gas curtain can be maintained within a larger vacuum environment. To keep the distance between the gas jet and localized pump as small as possible localized gas curtain 150 should be located close to the interaction between the electron beam 109 and the liquid metal anode 113. At this location, the electron beam 109 is focused as tightly as possible, so the distance between the gas jet and localized pump is minimized. However, the localized gas curtain 150 should be located sufficiently far from the interaction between the electron beam 109 and the liquid metal anode 113 to avoid disturbing the flow of liquid metal droplets. Similarly, localized gas curtain 151 should be located sufficiently close to the interaction between the electron beam 109 and the liquid metal anode 113 to keep the distance between the gas jet and localized pump as small as possible while protecting x-ray optics 119. In some embodiments, the distance between localized gas curtains 150 and 151 from the interaction between the electron beam 109 and the liquid metal anode 113 is less than one hundred millimeters. In some other embodiments, the distance between localized gas curtains 150 and 151 from the interaction between the electron beam 109 and the liquid metal anode 113 is less than ten millimeters.

In general, x-ray energy and generation efficiency scale with the elemental atomic number, Z, of the anode material. With some exceptions, the higher the atomic number, the higher the x-ray energy (i.e., shorter wavelength) and yield efficiency. Unfortunately, many materials having a relatively high atomic number also have high melting temperatures. FIG. 3 illustrates a chart 150 include a number of different candidate anode materials. By way of non-limiting example, the anode material could be any of the metals illustrated in FIG. 3, or any alloy of the metals (e.g., binary metal alloy, ternary metal alloy, etc.). In one example, a RuWMo alloy could be used as liquid droplet X-ray anode solid target.

Figure 2:
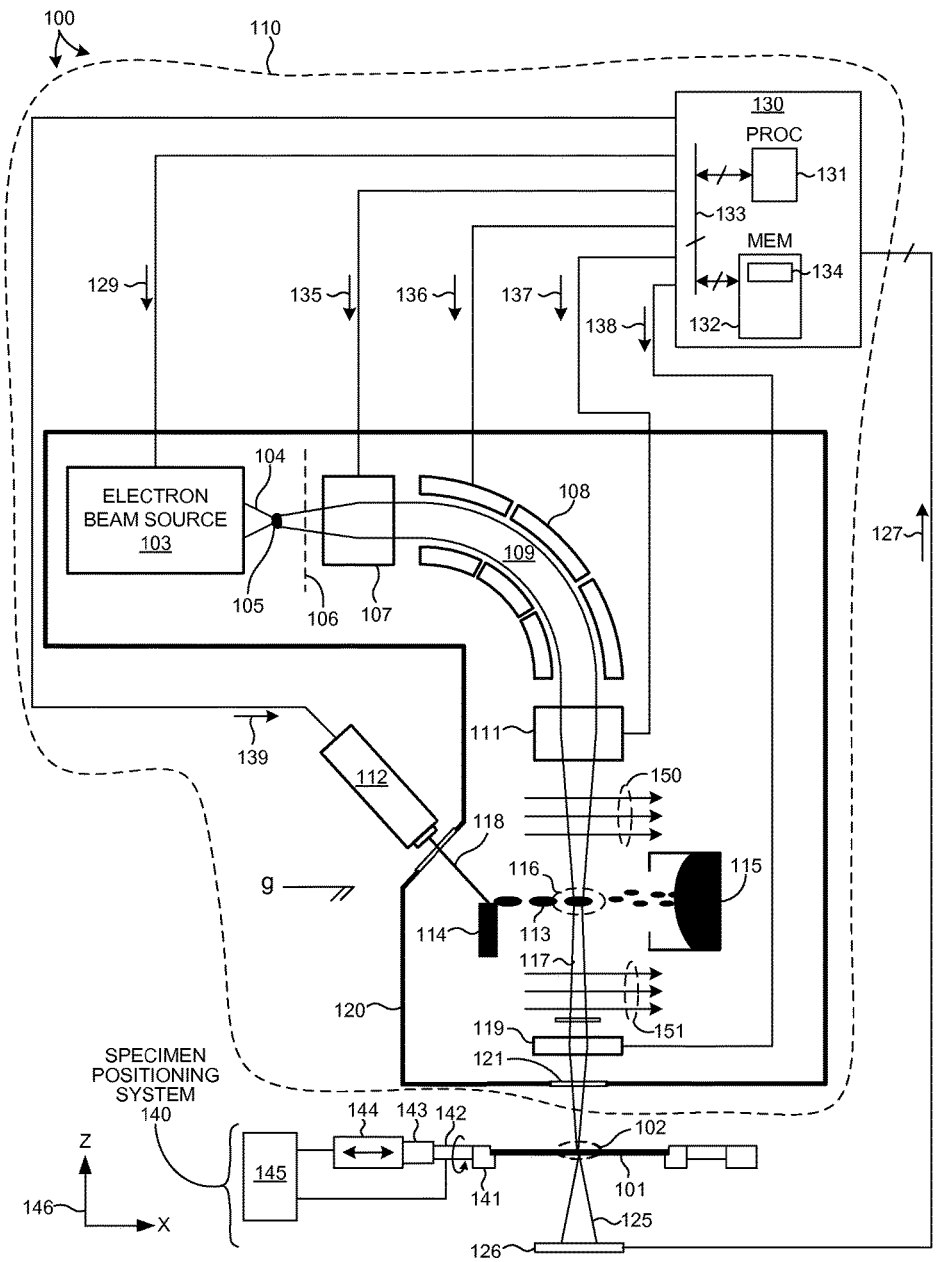
FIG. 2 is a diagram illustrative of an x-ray metrology system 100 for performing semiconductor metrology measurements including a LGLMD x-ray source 110 as described with reference to FIG. 1.
Figure 10:
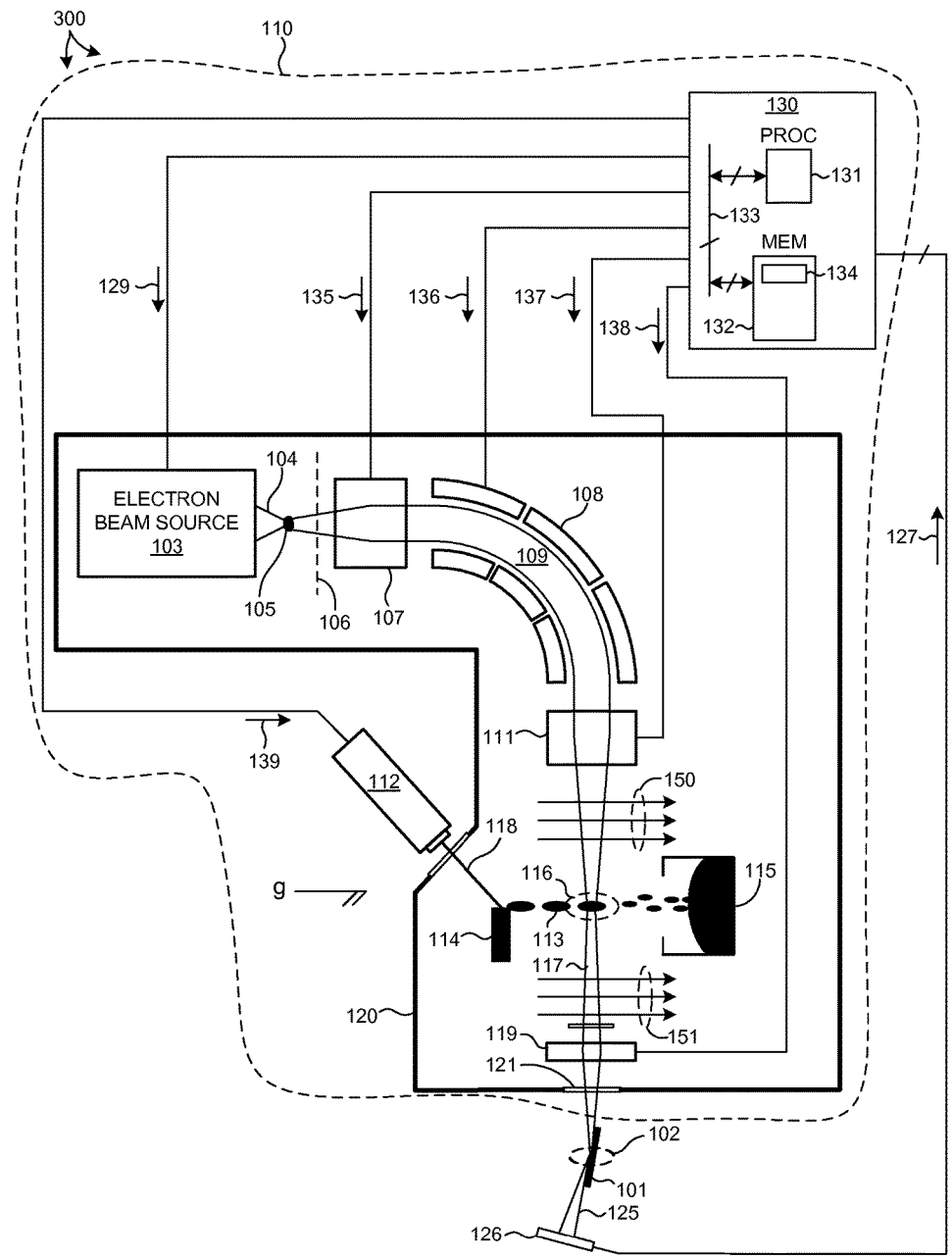
FIG. 10 is a diagram illustrative of an x-ray metrology system 300 for performing semiconductor metrology measurements including a LGLMD x-ray source 110 as described with reference to FIG. 1.

LGLMD x-ray source 110 includes a solid metal anode 114. A beam of laser light 118 emitted from laser 112 bombards solid metal anode 114 with high power. The interaction of the beam of laser light 118 with solid metal anode 114 causes localized heating and melting of a portion of the solid metal anode, forming liquid metal droplets. In some embodiments the melting temperature of the solid metal anode 114 is greater than 250 degrees Centigrade. In some embodiments, the melting temperature of the solid metal anode 114 is greater than 500 degrees Centigrade. The stream of liquid metal droplets 113 are directed into the path of the focused electron beam by gravity. As depicted in FIGS. 1, 2, and 10, the force of gravity is directed across the page from left to right, in line with the movement of liquid metal droplets from the solid metal anode 114 to the collector 115. The interaction between the focused, high energy electron beam and the stream of liquid metal droplets 113 generates x-ray emission 117. The remainder of the liquid metal droplets is collected in a liquid metal collector 115 where the droplets resolidify, and are ultimately removed from LGLMD x-ray source 110.

In some embodiments, laser 112 is a pulsed, continuous wavelength laser. In some embodiments, laser 112 is a femtosecond laser. In some examples, it is advantageous to use high-power, pulsed continuous wavelength lasers in the ultraviolet wavelength range (e.g., 532 nm or 355 nm). In some other examples, it may be desirable to use high-power, pulsed continuous wavelength lasers in the far infrared wavelength range (e.g., greater than 2,000 nm), such as a far infrared laser employing carbon dioxide ($CO_2$) as the working gas. These lasers are commonly available and currently employed in industrial material processing applications. In some other embodiments, high brightness direct diode lasers (e.g., 940 nanometer, 980 nanometer, 808 nanometer, etc.), or diode bars with fiber coupled or free space output may be employed to generate sufficient power densities to stimulate liquid metal droplets from solid metal anode 114. The aforementioned laser sources are provided by way of non-limiting example. In general, any laser light source with power density sufficient to melt the solid metal anode may be contemplated within the scope of this patent document.

In one example, the interaction between a solid Indium (Z=49) target and a beam of laser light emitted from a 150 kilohertz laser with a 20 ns pulse width and a laser fluence of 150 mJ/cm2 is simulated. The results indicate that such an interaction would bring the Indium target to a temperature above its melting point of 156° C. in less than a millisecond.

In another example, the interaction between a solid Tin (Z=50) target and a beam of laser light emitted from a 150 kilohertz laser with a 20 ns pulse width and a laser fluence of 250 mJ/cm2 is simulated. The results indicate that such an interaction would bring the Tin target to a temperature above its melting point of 232° C. in less than a millisecond.

In yet another example, the interaction between a solid Palladium (Z=46) target and a beam of laser light emitted from a 300 kilohertz laser with a 20 ns pulse width and a laser fluence of 1200 mJ/cm2 is simulated. The results indicate that such an interaction would bring the Palladium target to a temperature above its melting point of 1552° C. in less than a millisecond.

The average power of 2.25E4 W/cm2 required to melt the Indium target and the average power of 3.75E4 W/cm2 required to melt the Tin target can be achieved using conventional Nd:YAG ($\lambda$=1064 nm) lasers used in industrial material processing. For example, a Nd:YAG laser with an average power of 1 kW focused down to a 1 mm$^2$ spot size will yield an average power of 1E5 W/cm$^2$; more than sufficient to melt Indium or Tin. The average power of 3.6E5 W/cm2 required to melt the Palladium target can be achieved using conventional Ytterbium fiber lasers ($\lambda$=1070 nm) or disk lasers used in industrial material processing applications. A Ytterbium fiber laser with an average power of 10 kW focused down to a 1 mm$^2$ spot size will yield an average power of 1E7 W/cm$^2$; more than sufficient to melt Palladium. Similarly, available lasers should be sufficient to melt high Z metals and their alloys listed in FIG. 3.

In some embodiments, laser 112 is controlled to generate a stable flow of liquid metal droplets. In some embodiments, laser 112 is a pulsed, continuous wavelength laser. The pulse frequency determines the rate at which liquid metal droplets are generated. In addition, laser 112 may be configured for active control by computing system 130. As depicted in FIG. 1, computing system 130 is coupled to laser 112. Command signal 139 is communicated to laser 112. For example, the pulse frequency may be actively controlled based on command signal 139. In another example, the beam energy may be controlled based on command signal 139. In this manner, the size and frequency of liquid metal droplet generation may be controlled by computing system 113 to achieve a stable flow of liquid metal droplets having the desired size and repetition rate.

In a further aspect, the excitation source, e.g., either a high power density electron beam 109 or a high power density laser beam, is synchronized with the stream of liquid metal droplets such that high energy excitation pulses impinge on each liquid metal droplet to maximize the x-ray conversion efficiency. For example, electron beam source 103 may be configured for active control by computing system 130. As depicted in FIG. 1, computing system 130 is coupled to electron beam source 103. Command signal 129 is communicated to electron beam source 103. For example, a pulse frequency may be actively controlled based on command signal 129. In another example, the electron beam energy may be controlled based on command signal 129. In this manner, the timing and energy level may be synchronized with the stream of liquid metal droplets such that high energy excitation pulses impinge on each liquid metal droplet with maximum x-ray conversion efficiency.

In some embodiments, the liquid metal droplets have a diameter less than a few centimeters. In some embodiments, the liquid metal droplets have a diameter larger than a few nanometers. In some embodiments, the liquid metal droplets are produced at a frequency of a few Hz. In some other embodiments, the liquid metal droplets are produced continuously. A stable flow of consistently sized liquid metal droplets promotes uniform x-ray emission and reduced system noise.

In some embodiments, solid metal anode 114 is configured as a wire, ribbon, etc., and is passed through the path of the beam of laser light 118 by a metal dispensing system (not shown) at a desired speed to sustain the flow of liquid metal droplets. The stream of liquid metal droplets 113 includes one or more elements. By way of non-limiting example, the stream of liquid metal droplets 113 includes one of more of the elements listed in chart 150 of FIG. 3. In this manner, the stream of liquid metal droplets 113 produces x-ray lines corresponding with its constituent elements. In some embodiments, the LGLMD x-ray source 110 is configured to generate wavelengths between 0.01 nanometers and 1 nanometer. Exemplary methods and systems for generating high brightness, liquid metal x-ray illumination are described in U.S. Pat. No. 7,929,667, issued on Apr. 19, 2011, to KLA-Tencor Corp., the entirety of which is incorporated herein by reference.

Figure 5:
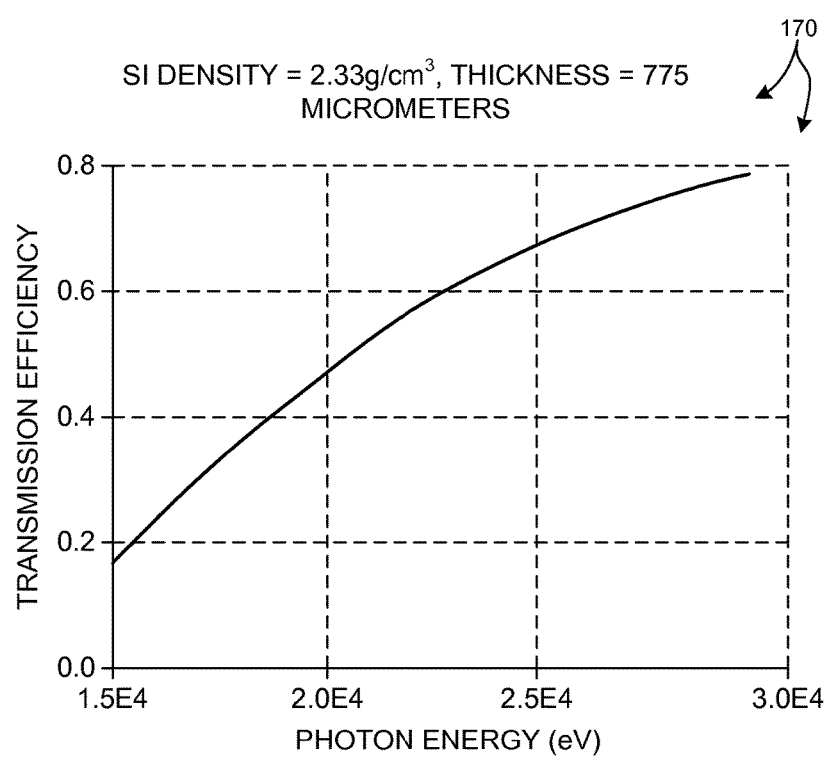
FIG. 5 depicts a plot 170 of the transmission efficiency of x-rays at different energy levels through a silicon wafer having a silicon density of 2.33 g/cm$^3$ and a thickness of 775 micrometers.

The coincidence of the liquid metal anode 113 and the stream of electrons 109 produces an x-ray beam 117 incident on inspection area 102 of specimen 101. In some embodiments, it is preferred to have an x-ray source photon energy greater than 24 keV. FIG. 5 depicts a plot 170 of the transmission efficiency of x-rays at different energy levels through a silicon wafer having a silicon density of 2.33 g/cm$^3$ and a thickness of 775 micrometers. As illustrated in plot 170, x-rays having an energy level greater than 24 keV penetrate through the silicon wafer with a transmission efficiency of greater than 70%. This transmission efficiency level is preferred for Transmission Small Angle X-ray Scattering (T-SAXS) based semiconductor metrology applications such as critical dimension and overlay metrology on patterned silicon wafers.

X-ray optics 119 shape and direct incident x-ray beam 117 to specimen 101. In some examples, x-ray optics 119 monochromatize the x-ray beam that is incident on the specimen 101. In some examples, x-ray optics 119 collimate or focus the x-ray beam 117 onto inspection area 102 of specimen 101. In some embodiments, x-ray optics 119 includes one or more x-ray collimating mirrors, x-ray apertures, x-ray monochromators, and x-ray beam stops, multilayer optics, refractive x-ray optics, diffractive optics such as zone plates, or any combination thereof.

In one further aspect, in-die metrology of semiconductor targets is enabled by high-brightness x-ray radiation focused to a small spot size. In some embodiments, advanced x-ray optics such as polycapillary x-ray optics, specular optics, or optics arranged in a Loxley-Tanner-Bowen configuration are employed to achieve high-brightness, small spot size illumination of a semiconductor specimen. For example, high intensity x-ray beams can be transported and focused to spot sizes of less than 40 micrometers using specular x-ray optics such as grazing incidence ellipsoidal mirrors, polycapillary optics such as hollow capillary x-ray waveguides, multilayer optics, or crystalline optics such as a Loxley-Tanner-Bowen system. Exemplary optical systems for transmission and focusing of high intensity x-ray beams are described by D. K. Bowen and B. K. Tanner in "High Resolution X-Ray Diffractometry and Topography," Taylor and Francis, London, 1998, the entirety of which is incorporated herein by reference.

In addition, in some embodiments, multilayer optics are employed to monochromatize the x-ray beam 117 to a spectral purity, $\delta\lambda/\lambda$, of less than $10^{-1}$. This level of spectral purity is suitable for metrology technologies such as x-ray reflectivity (XRR), x-ray diffraction (XRD), and x-ray fluorescence (XRF). In some other embodiments, crystal monochromators are employed to monochromatize the x-ray beam 117 to a spectral purity, $\delta\lambda/\lambda$, of less than $10^{-6}$. This level of spectral purity is suitable for metrology technologies such as high resolution x-ray diffraction (HRXRD).

X-ray optics 119 may be configured for active control by computing system 130. As depicted in FIG. 1, computing system 130 is coupled to x-ray optics 119. Command signal 138 is communicated to x-ray optics 119 from computing system 130. For example, the position of an optical element may be manipulated by a positioning system (not shown) based on command signal 138. In this manner, the focusing and directing of the x-ray beam 117 is achieved under the control of computing system 130 to achieve a stable illumination incident on specimen 101. In some examples, computing system 130 is configured to control the positioning and spot size of the x-ray beam 117 incident on specimen 101. In some examples, computing system 130 is configured to control illumination properties of the x-ray beam 117 (e.g., intensity, polarization, spectrum, etc.).

In some embodiments, a localized gas purge is directed onto specimen 101 to further reduce noise introduced into the x-ray beam 117 by environmental disturbances.

In some embodiments, the LGLMD x-ray source 110 is maintained in the same atmospheric environment as specimen 101 (e.g., gas purge environment). However, in some embodiments, the distance between specimen 101 and electron beam source 103 is lengthy (e.g., greater than one meter). In these embodiments, environmental disturbances (e.g., air turbulence) contribute noise to the illumination light and detected signals. Hence in some embodiments, portions of LGLMD x-ray source 110 (e.g., any of electron beam source 103, electron optics 107, 108, and 111, stream of liquid metal droplets 113, and x-ray optics 119) are maintained in a localized vacuum environment separated from the specimen by vacuum windows. For example, as depicted in FIG. 1, a vacuum environment is maintained within vacuum chamber 120 that contains many elements of LGLMD x-ray source 110. These elements are separated from specimen 101 by a vacuum window 121. In the embodiment depicted in FIG. 1, x-ray optics 119 is located within vacuum chamber 120. However, in some other embodiments, x-ray optics 119 is located outside of vacuum chamber 120, between window 121 and specimen 101.

Figure 6:
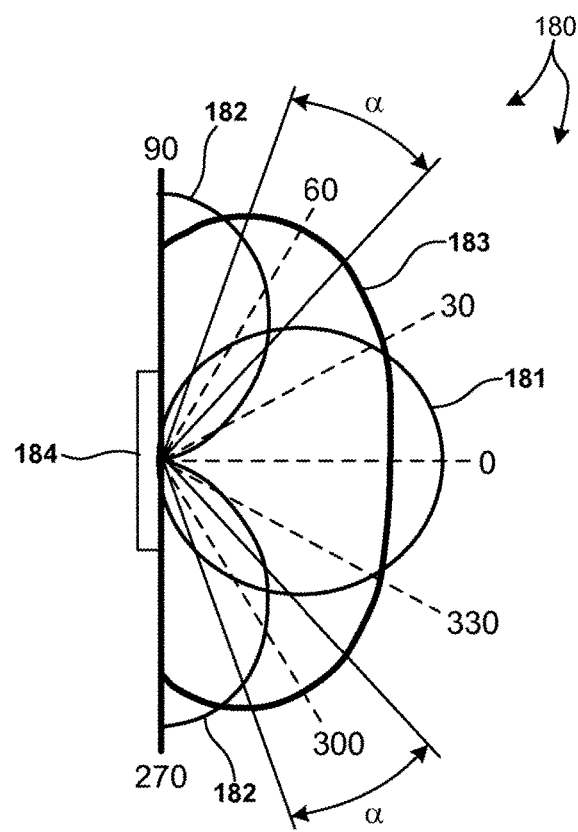
FIG. 6 depicts a simulation of the intensity distribution of x-ray emission from an anode surface.

In another aspect, x-ray optics 119 are configured at specific collection angles to capture x-ray emission in the desired energy band at peak intensity. When a high energy focused electron beam impinges upon a metal anode target (either solid or liquid), the stimulated x-ray emission includes broadband Bremsstrahlung radiation and characteristic line emission (i.e., Kα, Kβ, Lα, Lβ, etc.). Although, Bremsstrahlung radiation emission is typically Lambertian, the angular distribution of line emission is typically anisotropic. For example, FIG. 6 depicts a simulation of the intensity distribution of x-ray emission from anode surface 184. As depicted, plotline 181 depicts a Lambertian Bremsstrahlung emission from anode surface 184. In addition, plotlines 182 depict a dipole distribution of Kα line emission from anode surface 184. Plotline 183 depicts the superposition of Bremsstrahlung emission and Kα line emission from anode surface 184. As illustrated, peak intensity is achieved over a range of collection angles, α, centered around the peak intensity of the superposition of the Bremsstrahlung emission and the desired line emission (e.g., Kα). In the depicted example, peak intensity is realized approximately sixty degrees from the normal to anode surface 184. In some embodiments, x-ray collection optics are oriented in such a way as to optimize x-ray brightness by collecting x-ray radiation over the range of collection angles, α. In some examples, α, is less than twenty degrees. In some other examples, α, is less than ten degrees.

In some embodiments, x-ray optics are designed to directly focus radiation of the strongest x-ray line emissions to the measurement target. However, in some other embodiments, x-ray optics are designed to focus radiation of the strongest X-ray line emissions onto a secondary target. The secondary target produces x-ray lines of the constituent elements of the secondary target. The emission from the secondary target is subsequently focused onto the measurement target. In this manner, the x-ray energy produced by LGLMD 101 is modified before reaching the measurement target. Such an approach may be employed to reduce the level of background broadband radiation. By way of non-limiting example, peak x-ray fluorescence (XRF) measurement values are sometimes unable to be resolved due to background noise caused by bremsstrahlung emission. In some embodiments, a secondary target is employed to filter out the bremsstrahlung emission, thus allowing the peak values to be resolved. Materials suitable as secondary targets include any material having a longer x-ray wavelength compared to the primary target.

FIG. 2 illustrates an x-ray metrology system 100 for performing semiconductor metrology measurements. By way of non-limiting example, x-ray metrology system 100 operates in a transmission mode. X-ray metrology system 100 includes LGLMD x-ray source 110 as described with reference to FIG. 1. As illustrated in FIG. 2, x-ray metrology system 100 includes similar, like numbered elements described with reference to FIG. 1. The high energy nature of x-ray radiation allows for the penetration of x-rays into optically opaque thin films, buried structures, high-aspect ratio structures and devices containing many thin film layers. LGLMD x-ray source 110 with higher electron beam power density delivers higher brightness and increased x-ray flux interacting with the specimen. In addition, LGLMD x-ray source 110 with a low noise electron source, stable stream of liquid metal droplets, low noise electron beam optics, and high efficiency x-ray optics delivers x-ray illumination to the specimen with reduced noise. X-ray metrology system 100 is configured such that x-rays which interact with the specimen are collected by a detector while a sample handler positions the specimen to produce angularly resolved interactions of the sample with the x-rays. In addition any other particles produced during the interaction such as photoelectrons, x-rays produced through fluorescence, or ions can be detected.

As depicted in FIG. 2, x-ray detector 126 collects x-ray radiation 125 scattered from specimen 101 and generates an output signal 127 indicative of properties of specimen 101 that are sensitive to the incident x-ray radiation. Scattered x-rays 125 are collected by x-ray detector 126 while specimen positioning system 140 locates and orients specimen 101 to produce angularly resolved scattered x-rays. The x-ray detector 126 is able to resolve one or more x-ray photon energies and produces signals for each x-ray energy component indicative of properties of the specimen. In some embodiments, the x-ray detector 126 includes any of a CCD array, a microchannel plate, a photodiode array, a microstrip proportional counter, a gas filled proportional counter, and a scintillator. In some embodiments, single photon counting detectors with high dynamic range increase the signal to noise ratio of output signal 127.

Figure 4:
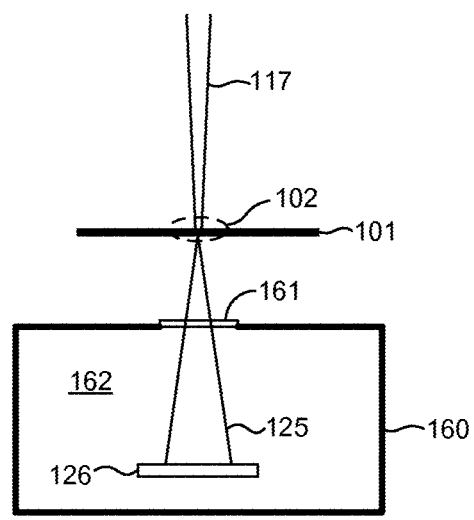
FIG. 4 is a diagram illustrative of an x-ray detector 126 of x-ray metrology system 100 contained in a vacuum environment 162 separate from specimen 101.

In some embodiments, the x-ray detector is maintained in the same atmospheric environment as specimen 101 (e.g., gas purge environment). However, in some embodiments, the distance between specimen 101 and x-ray detector 126 is lengthy (e.g., greater than one meter). In these embodiments, environmental disturbances (e.g., air turbulence) contribute noise to the detected signals. Hence in some embodiments, the x-ray detector is maintained in a localized, vacuum environment separated from the specimen (e.g., specimen 101) by a vacuum window. FIG. 4 is a diagram illustrative of a vacuum chamber 160 containing x-ray detector 126. In a preferred embodiment, vacuum chamber 160 includes a substantial portion of the path between specimen 101 and x-ray detector 126. An opening of vacuum chamber 160 is covered by vacuum window 161. Vacuum window 161 may be constructed of any suitable material that is substantially transparent to x-ray radiation (e.g., Beryllium). Scattered x-ray radiation 125 passes through vacuum window 161, enters vacuum chamber 160 and is incident on x-ray detector 126. A suitable vacuum environment 162 is maintained within vacuum chamber 160 to minimize disturbances to scattered x-ray radiation 125.

FIG. 10 illustrates an x-ray metrology system 300 for performing semiconductor metrology measurements. By way of non-limiting example, x-ray metrology system 300 operates in a grazing incidence mode. More specifically, x-ray metrology system 300 is configured as a grazing incidence small-angle x-ray scattering (GISAXS) measurement system. Typical angles of incidence and collection are approximately one degree as measured from the surface of the specimen, or approximately eighty nine degrees from an axis normal to the surface of the specimen. X-ray metrology system 300 includes LGLMD x-ray source 110 as described with reference to FIG. 1. As illustrated in FIG. 10, x-ray metrology system 300 includes similar, like numbered elements described with reference to FIGS. 1 and 2. X-ray metrology system 300 is configured such that x-rays which are scattered from the specimen are collected by a detector while a sample handler (not shown) positions the specimen. In addition any other particles produced during the interaction such as photoelectrons, x-rays produced through fluorescence, or ions can be detected. Metrology systems configured to perform GISAXS measurements require a high brightness x-ray source to maintain sufficient brightness over the relatively large sample area illuminated at small angles. For this reason, LGLMD x-ray source 110 is particularly well suited for GISAXS measurements.

By way of non-limiting example, the x-ray metrology system 100 illustrated in FIG. 2 is configured as a transmission small angle x-ray scatterometer (TSAXS) and the x-ray metrology system 300 illustrated in FIG. 10 is configured as a grazing incidence small angle x-ray scatterometer (GISAXS). However, in general x-ray metrology system 100 employing a high brightness liquid metal jet x-ray source as described herein may employ any one or more of the following metrology techniques: transmission small angle x-ray scattering (TSAXS), grazing incidence small angle x-ray scattering (GISAXS), wide angle x-ray scattering (WAXS), x-ray reflectivity (XRR), x-ray diffraction (XRD), grazing incidence x-ray diffraction (GIXRD), high resolution x-ray diffraction (HRXRD), x-ray photoelectron spectroscopy (XPS), x-ray fluorescence (XRF), grazing incidence x-ray fluorescence (GIXRF), x-ray tomography, x-ray ellipsometry, and hard x-ray photoemission spectrometry (HXPS).

X-ray metrology tool 100 also includes computing system 130 employed to acquire signals 127 generated by x-ray detector 126 and determine properties of the specimen based at least in part on the acquired signals. As illustrated in FIG. 2, computing system 130 is communicatively coupled to x-ray detector 126. In one example, x-ray detector 126 is an x-ray spectrometer and measurement data 127 includes an indication of the measured spectral response of the specimen based on one or more sampling processes implemented by the x-ray spectrometer. Computing system 130 is configured to build models of the specimen, create x-ray simulations based upon the models, and analyze the simulations and signals received from x-ray detector 126 to determine one or more characteristics of the sample.

In a further embodiment, computing system 130 is configured to access model parameters in real-time, employing Real Time Critical Dimensioning (RTCD), or it may access libraries of pre-computed models for determining a value of at least one specimen parameter value associated with the specimen 101. In general, some form of CD-engine may be used to evaluate the difference between assigned CD parameters of a specimen and CD parameters associated with the measured specimen. Exemplary methods and systems for computing specimen parameter values are described in U.S. Pat. No. 7,826,071, issued on Nov. 2, 2010, to KLA-Tencor Corp., the entirety of which is incorporated herein by reference.

In one example, measurement data 127 includes an indication of the measured x-ray response of the specimen. Based on the distribution of the measured x-ray response on the surface of detector 126, the location and area of incidence of x-ray beam 117 on specimen 101 is determined by computing system 130. In one example, pattern recognition techniques are applied by computing system 130 to determine the location and area of incidence of x-ray beam 117 on specimen 101 based on measurement data 127. In response computing system 130 generates any of command signals 135, 136, 137, and 138 to electron optics 107, beam bending optics 108, electron optics 111, and x-ray optics 119, respectively, to redirect and reshape incident x-ray illumination beam 117.

In another aspect, x-ray measurements of a particular inspection area are performed at a number of different out of plane orientations. This increases the precision and accuracy of measured parameters and reduces correlations among parameters by extending the number and diversity of data sets available for analysis to include a variety of large-angle, out of plane orientations. Measuring specimen parameters with a deeper, more diverse data set also reduces correlations among parameters and improves measurement accuracy.

As illustrated in FIG. 2, x-ray metrology tool 100 includes a specimen positioning system 140 configured to both align specimen 101 and orient specimen 101 over a large range of out of plane angular orientations with respect the LGLMD x-ray source. In other words, specimen positioning system 140 is configured to rotate specimen 101 over a large angular range about one or more axes of rotation aligned in-plane with the surface of specimen 101. In some embodiments, specimen positioning system 140 is configured to rotate specimen 101 within a range of at least 90 degrees about one or more axes of rotation aligned in-plane with the surface of specimen 101. In some embodiments, specimen positioning system is configured to rotate specimen 101 within a range of at least 60 degrees about one or more axes of rotation aligned in-plane with the surface of specimen 101. In some other embodiments, specimen positioning system is configured to rotate specimen 101 within a range of at least one degree about one or more axes of rotation aligned in-plane with the surface of specimen 101. In this manner, angle resolved measurements of specimen 101 are collected by x-ray metrology system 100 over any number of locations on the surface of specimen 101. In one example, computing system 130 communicates command signals to motion controller 145 of specimen positioning system 140 that indicate the desired position of specimen 101. In response, motion controller 145 generates command signals to the various actuators of specimen positioning system 140 to achieve the desired positioning of specimen 101. By way of non-limiting example, a specimen positioning system may include any combination of a hexapod, linear, and angular stages.

By way of non-limiting example, as illustrated in FIG. 2, specimen positioning system 140 includes an edge grip chuck 141 to fixedly attach specimen 101 to specimen positioning system 140. A rotational actuator 142 is configured to rotate edge grip chuck 141 and the attached specimen 101 with respect to a perimeter frame 143. In the depicted embodiment, rotational actuator 142 is configured to rotate specimen 101 about the x-axis of the coordinate system 146 illustrated in FIG. 1. As depicted in FIG. 2, a rotation of specimen 101 about the z-axis is an in plane rotation of specimen 101. Rotations about the x-axis and the y-axis (not shown) are out of plane rotations of specimen 101 that effectively tilt the surface of the specimen with respect to the metrology elements of metrology system 100. Although it is not illustrated, a second rotational actuator is configured to rotate specimen 101 about the y-axis. A linear actuator 144 is configured to translate perimeter frame 143 in the x-direction. Another linear actuator (not shown) is configured to translate perimeter frame 143 in the y-direction. In this manner, every location on the surface of specimen 101 is available for measurement over a range of out of plane angular positions. For example, in one embodiment, a location of specimen 101 is measured over several angular increments within a range of −45 degrees to +45 degrees with respect to the normal orientation of specimen 101.

The large, out of plane, angular positioning capability of specimen positioning system 140 expands measurement sensitivity and reduces correlations between parameters. For example, in a normal orientation, SAXS is able to resolve the critical dimension of a feature, but is largely insensitive to sidewall angle and height of a feature. However, collecting measurement data over a broad range of out of plane angular positions enables the collection of measurement data associated with a number of diffraction orders. This enables the sidewall angle and height of a feature to be resolved. In addition, other features such as rounding or any other shapes associated with advanced structures can be resolved.

A x-ray metrology tool employing a high brightness liquid metal droplet x-ray source as described herein enables increased measurement sensitivity and throughput due to the high brightness and short wavelength radiation (e.g., 0.01-1 nanometers) generated by the source. By way of non-limiting example, the x-ray metrology tool is capable of measuring geometric parameters (e.g., pitch, critical dimension (CD), side wall angle (SWA), line width roughness (LWR), and line edge roughness (LER)) of structures smaller than 10 nanometers. In addition, the high energy nature of x-ray radiation penetrates optically opaque thin films, buried structures, high aspect ratio structures, and devices including many thin film layers.

A x-ray metrology system employing a high brightness liquid metal jet x-ray source as described herein may be used to determine characteristics of semiconductor structures. Exemplary structures include, but are not limited to, Fin-FETs, low-dimensional structures such as nanowires or graphene, sub 10 nm structures, thin films, lithographic structures, through silicon vias (TSVs), memory structures such as DRAM, DRAM 4F2, FLASH and high aspect ratio memory structures. Exemplary structural characteristics include, but are not limited to, geometric parameters such as line edge roughness, line width roughness, pore size, pore density, side wall angle, profile, film thickness, critical dimension, pitch, and material parameters such as electron density, crystalline grain structure, morphology, orientation, stress, and strain.

It should be recognized that the various steps described throughout the present disclosure may be carried out by a single computer system 130 or, alternatively, a multiple computer system 130. Moreover, different subsystems of the system 100, such as the specimen positioning system 140, may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the x-ray detector 126, electron optics 107, 108, and 111, x-ray optics 119, electron beam source 103, and laser 112 in any manner known in the art. For example, the one or more computing systems 130 may be coupled to computing systems associated with the x-ray detector 126, electron optics 107, 108, and 111, x-ray optics 119, electron beam source 103, and laser 112, respectively. In another example, any of the x-ray detector 126, electron optics 107, 108, and 111, x-ray optics 119, electron beam source 103, and laser 112 may be controlled directly by a single computer system coupled to computer system 130.

The computer system 130 of the x-ray metrology system 100 may be configured to receive and/or acquire data or information from the subsystems of the system (e.g., x-ray detector 126, electron optics 107, 108, and 111, x-ray optics 119, electron beam source 103, and laser 112, and the like) by a transmission medium that may include wireline and/or wireless portions. In this manner, the transmission medium may serve as a data link between the computer system 130 and other subsystems of the system 100.

Computer system 130 of the combined metrology system 100 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 100, external memory, or external systems). For example, the computing system 130 may be configured to receive measurement data (e.g., output signals 127) from a storage medium (i.e., memory 132) via a data link. For instance, spectral results obtained using a spectrometer of x-ray detector 126 may be stored in a permanent or semi-permanent memory device (e.g., memory 132). In this regard, the spectral results may be imported from on-board memory or from an external memory system. Moreover, the computer system 130 may send data to other systems via a transmission medium. For instance, specimen parameter values determined by computer system 130 may be stored in a permanent or semi-permanent memory device. In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 1, program instructions stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

In some embodiments, x-ray metrology as described herein is implemented as part of a fabrication process tool. Examples of fabrication process tools include, but are not limited to, lithographic exposure tools, film deposition tools, implant tools, and etch tools. In this manner, the results of x-ray measurements are used to control a fabrication process. In one example, x-ray measurement data collected from one or more targets is sent to a fabrication process tool. The x-ray data is analyzed and the results used to adjust the operation of the fabrication process tool.

Figure 9:
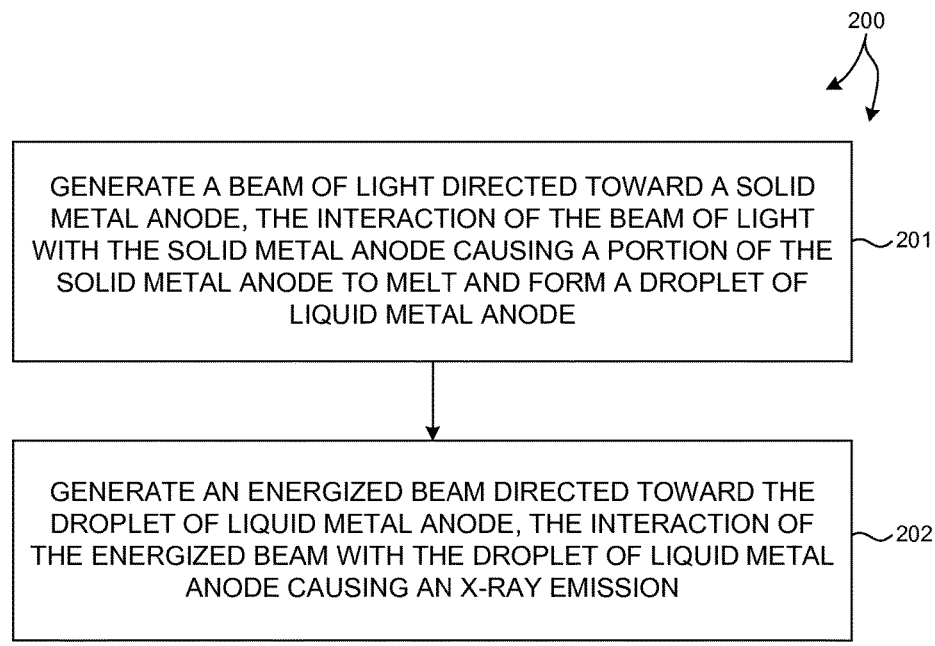
FIG. 9 is a flowchart illustrative of an exemplary method 200 suitable for generating x-ray emission from liquid metal droplets.

FIG. 9 illustrates a method 200 suitable for implementation by the x-ray metrology system 100 of the present invention. In one aspect, it is recognized that any data processing elements of method 200 may be carried out via a pre-programmed algorithm executed by one or more processors of computing system 130. While the following description is presented in the context of x-ray metrology system 100, it is recognized herein that the particular structural aspects of x-ray metrology system 100 do not represent limitations and should be interpreted as illustrative only.

In block 201, a beam of light is generated and directed toward a solid metal anode. The interaction of the beam of light with the solid metal anode causes a portion of the solid metal anode to melt and form a droplet of liquid metal anode.

In block 202, an energized beam is generated and directed toward the droplet of liquid metal anode. The interaction of the energized beam with the droplet of liquid metal anode causes an x-ray emission.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including critical dimension applications and overlay metrology applications. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from a liquid droplet x-ray source.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A liquid metal droplet illumination source, comprising:
   a laser configured to emit a beam of light toward a solid metal anode, the interaction of the beam of light with the solid metal anode causing a portion of the solid metal anode to melt and form a droplet of liquid metal anode;
   an excitation source configured to emit an energized beam directed toward the droplet of liquid metal anode, the interaction of the energized beam with the droplet of liquid metal anode causing an x-ray emission; and
   at least one x-ray optical element configured to collect an amount of the x-ray emission over a range of angles from a surface normal of the liquid metal anode, wherein the range of angles includes an angle of maximum intensity of a superposition of Bremsstrahlung emission and a desired line emission.

2. The liquid metal droplet illumination source of claim 1, wherein the excitation source is an electron source configured to emit a stream of electrons from a cathode of the electron source.

3. The liquid metal droplet illumination source of claim 1, wherein the laser is a pulsed laser.

4. The liquid metal droplet illumination source of claim 1, further comprising:
   a localized flow of gas located in a path of the energized beam near the interaction of the energized beam with the droplet of liquid metal anode.

5. The liquid metal droplet illumination source of claim 1, further comprising:

a localized flow of gas located in a path of the x-ray emission between the interaction of the energized beam with the droplet of liquid metal anode and the at least one x-ray optical element.

6. The liquid metal droplet illumination source of claim 1, wherein a melting temperature of the solid metal anode is greater than two hundred fifty degrees Centigrade.

7. The liquid metal droplet illumination source of claim 2, wherein an electron beam power density of the stream of electrons exceeds 1,000 kilowatts per millimeter squared at impact with the droplet of liquid metal anode.

8. The liquid metal droplet illumination source of claim 1, further comprising:
a computing system configured to communicate a first control signal to at least one electron optical element, wherein the at least one electron optical element is configured to focus a stream of electrons toward the liquid metal anode in response to the first control signal, and wherein the computing system is also configured to communicate a second control signal to at least one x-ray optical element, wherein the at least one x-ray optical element is configured to focus an amount of x-ray radiation generated by the interaction of the stream of electrons with the liquid metal anode toward a specimen in response to the second control signal.

9. The liquid metal droplet illumination source of claim 1, further comprising:
a computing system configured to communicate a first control signal to the excitation source, wherein the excitation source generates a high power density excitation beam synchronized with a stream of liquid metal droplets.

10. An x-ray metrology system comprising:
a liquid metal droplet based x-ray illumination source configured to illuminate an inspection area of a specimen with an incident x-ray beam, wherein the liquid metal droplet based x-ray illumination source includes,
a laser configured to emit a beam of light toward a solid metal anode, the interaction of the beam of light with the solid metal anode causing a portion of the solid metal anode to melt and form a stream of droplets of liquid metal anode;
an excitation source configured to emit an energized beam directed toward the stream of droplets of liquid metal anode, the interaction of the energized beam with the stream of droplets of liquid metal anode causing an x-ray emission; and
at least one x-ray optical element configured to collect an amount of the x-ray emission over a range of angles from a surface normal of the liquid metal anode, wherein the range of angles includes an angle of maximum intensity of a superposition of Bremsstrahlung emission and a desired line emission; and
an x-ray detector configured to receive radiation from the specimen in response to the incident x-ray beam and generate signals indicative of a first property of the specimen.

11. The x-ray metrology system of claim 10, wherein the excitation source is an electron source configured to emit a stream of electrons from a cathode of the electron source, wherein an electron beam power density of the stream of electrons exceeds 1,000 kilowatts per millimeter squared at impact with the liquid metal anode.

12. The x-ray metrology system of claim 10, further comprising:
a localized flow of gas located in a path of the energized beam near the interaction of the energized beam with the droplet of liquid metal anode.

13. The x-ray metrology system of claim 10, further comprising:
a localized flow of gas located in a path of the x-ray emission between the interaction of the energized beam with the droplet of liquid metal anode and the at least one x-ray optical element.

14. The x-ray metrology system of claim 10, further comprising:
a computing system configured to communicate a first control signal to the excitation source, wherein the excitation source generates a high power density excitation beam synchronized with the stream of liquid metal droplets.

15. The x-ray metrology tool of claim 10, wherein a melting temperature of the solid metal anode is greater than two hundred fifty degrees Centigrade.

16. The x-ray metrology tool of claim 10, wherein the x-ray metrology tool is a small angle x-ray scattering metrology tool configured to perform critical dimension measurements.

17. The x-ray metrology tool of claim 10, wherein the x-ray metrology tool is a small angle x-ray scattering metrology tool configured to perform overlay measurements.

18. A method comprising:
generating a beam of light directed toward a solid metal anode, the interaction of the beam of light with the solid metal anode causing a portion of the solid metal anode to melt and form a droplet of liquid metal anode;
generating an energized beam directed toward the droplet of liquid metal anode, the interaction of the energized beam with the droplet of liquid metal anode causing an x-ray emission; and
collecting an amount of the x-ray emission over a range of angles from a surface normal of the liquid metal anode, wherein the range of angles includes an angle of maximum intensity of a superposition of Bremsstrahlung emission and a desired line emission.

19. The method of claim 18, further comprising:
shielding an element of a source of the energized beam from the interaction of the energized beam with the droplet of liquid metal anode with a localized gas curtain.

* * * * *